United States Patent [19]
Watanabe et al.

[11] Patent Number: 4,777,946
[45] Date of Patent: Oct. 18, 1988

[54] PATELLA BRACE

[75] Inventors: Tetsuya Watanabe; Toshiro Nakamura, both of Shimane, Japan

[73] Assignee: Nakamura Brace Co., Ltd., Japan

[21] Appl. No.: 820,185

[22] Filed: Jan. 17, 1986

[30] Foreign Application Priority Data

Nov. 20, 1985 [JP] Japan .................... 60-262255

[51] Int. Cl.⁴ .................................... A61F 13/00
[52] U.S. Cl. .................... 128/157; 128/882
[58] Field of Search .................... 128/78, 80 C, 80 G, 128/87 A, 87 R, 77, 133, 157, 165, DIG. 15, DIG. 20; 2/16, 18, 24

[56] References Cited

U.S. PATENT DOCUMENTS

| 3,373,741 | 3/1968 | Hill et al. ............................. | 128/157 |
| 3,782,378 | 1/1974 | Page ..................................... | 128/133 |
| 3,823,713 | 7/1974 | Shah ..................................... | 128/157 |
| 3,926,186 | 12/1975 | Nirschl ............................... | 128/80 R |
| 4,342,185 | 8/1982 | Pellew ................................. | 128/80 R |

*Primary Examiner*—Gregory E. McNeill
*Attorney, Agent, or Firm*—Darby & Darby

[57] ABSTRACT

A gadget for remedy and prevention of knee joint trouble accompanied by the movement of the patella, comprising a patella fixing member and a connecting belt wound round the knee to fix the patella fixing member thereon. The patella fixing member is provided with an opening for exposing the patella. A distinguishing feature is the provision of a fixing member pressing band on the top side of the fixing member covering the opening to prevent the decrease of correction effect due to the deformation of the opening being extended when the brace is put on and when the knee joint is bent.

11 Claims, 3 Drawing Sheets

PATELLA BRACE

BACKGROUND OF THE INVENTION

Field of the Invention

The present invention relates to a patella brace used in the gadget therapy of patella/thighbone troubles, particularly in the outside dislocation of patella, for the protection, correction and removal of pains. More particularly, it relates to the gadget for preventing the troubles of kneejoints in sports such as volleyball and basketball in which kneejoints usually undergo excessive physical burdens.

Troubles of patella/thighbone should be treated in accordance with the individual condition of the patients, that is, the type and degree of the trouble. Operations of tha patient in serious troubles have been thoroughly studied and are being well attended, while the preservative therapy of less serious nature of troubles are, particularly the gadget therapy are not beint taken up for studies with sufficient seriousness and no remedy worth mentioning has been accorded.

It is so said because of the drawbacks of the conventional patella brace which restricts the patient's physical movements, giving great inconveniences in daily life and causing functional obstacles to other positions of the body, and that its wearing is especially disliked by women for calisthenic reason. Many girls participate in the sport club activities such as of volleyball and basketball these days in junior and senior high schools. Some of them are suffering from patella troubles. The symptom in most of these cases is that the patella moves to the outside laterally (toward the gastrocnemius side or a little upward). There are many cases in which the reason of their occurance and causes are not clear as to why it concentrates on girls. And any fundamentally effective therapy is not known yet, and the only method usually used is to wear a therapeutical gadget for correcting the dislocation of patella. Such a gadget is, however, generally bulky, difficult to handle, with a feeling of unfitness and sense of incompatibility, and disagreeable in appearance.

The knee joint is situated between the bottom end of the thighbone and the top end of the shinbone behind the patella. These bones are jointed together by many ligaments such as the joint capsule, inside and outside accessory ligaments, and cruciate ligament in the joint cavity, and are limited in direction and range of motion by these ligaments.

Since the reinforcements by these muscles are very powerful (this is readily proven by the fact that a fracture of bone is more apt to occur than a dislocation of joint by an external injury), the balance in reinforcement strength may be badly broken, affecting directly other parts when a trouble occurs. The most vulnerable point to it is the patella. When a therapy is to be applied to cure a subluxation of patella or fracture of patella by putting on a gadget, all bones and muscles concerned are moved or varied in position in complicated manner as the knee is bent or stretched. Thus, it is difficult to fix these parts and almost impossible to make therapy by mere forced pulling.

The conventional knee braces are roughly classified into two kinds. Among them the fixing-by-winding type fixes the upper and lower parts of the knee joint, that is, the lower part of the thigh and the upper part of the crus and confines the patella in position by the strong fixing force.

The cylindrical type is composed of an elastic fabric having a sufficient stretchability to allow the foot and the heel to pass through when it is put on or taken off. It is rather superior in giving mobility to the body than the general fixing-by-winding type and is widely used as knee supporters for sporting use.

In any case, the conventional gadgets are large in size excepting those supporters for sport use which are hardly expectable to be of any effectiveness for the therapy use. The fixing-by-winding type, in particular, which must be firmly secured in the upper and lower portions of the knee joint is conspicuous in this trend. It is not suitable as a gadget for therapy in view of the fact that the gadget therapy requires a longer period than others such as the operational therapy. The cylindrical type, despite its drawback in that its correcting effect is smaller, is certainly suitable for the sportsmen who move vigorously, because it is difficult to drop off once put on. However, for patients of patella, particularly for those who need not be helped by other persons in daily behaviors, the cylindrical gadget is very inconvenient, because it is necessary for putting on the gadget to bend the body or the leg deeply. Furthermore, it is difficult to decrease the pressure of the cylindrical brace on the patella gradually as the curing therapy proceeds.

In consideration of these points, the inventors designed previously a brace which had the advantages of fixing-by-winding type and removing the drawbacks of the cylindrical type.

This had a configuration 25 as shown in FIG. 5, comprising a fixing member 21 having an opening 20 for exposing the patella, and connecting belts 22, 22 extending from both the ends of the fixing parts 21 respectively, so as to apply an adequate tension to the patella. The embodiment in FIG. 5 contains a fixing means made of silicone rubber for the fixing part.

This brace had various advantages such as it is very easy in attaching as well as in detaching, giving scarcely any feel of incompatibility while putting on, being compact in size and light in weight, accompanying no musty feel due to perspiration, and that the pressure on the affected part can be adjusted as required according to the stage of progress of therapy. However, a number of problems were found by the studies and test uses afterwards. They are: (1) when the brace is applied to the affected part, with the expansion of the fixing member for exposing the patella the dislocation of the opening takes place from the knee joint part resulting in decreased pressure on the patella, and (2) the brace cannot cope with the minute difference in the direction of pressure to be applied from a patient to another. Against these problems, remedies had to be taken especially with regard to (1) for a fundamental improvement.

SUMMARY OF THE INVENTION

As the result of steady and tireless studies by the inventors, an ideal patella brace has been developed. This brace is characterized in that it is provided with a band for pressing the patella fixing member on the top face of the patella fixing member along the longitudinal direction of the connecting belt, and on the bottom face of the fixing member pressing band with a patch for pressing the patella. This is to hold down the patella fixing member which is deformed along the knee joint line when the brace is applied, so that the opening in the fixing member may not depart from the knee joint part.

In addition, the patella pressing patch defines the the direction of pressure to be applied on the knee joint.

The term "patella fixing member" used in this specification means a member of the brace covering the front face of the knee joint. It is provided in its center with an opening for exposing the patella. It assures the movement of patella, but does not fix it in the pressing direction. It is attached with a connecting belts at both ends, but they are not limited in their configuration, material, etc. On the top side of the patella fixing member, a fixing member pressing band is attached. It is preferably made of a tough material and the fixing position of both ends are preferably spaced apart because it is to prevent the departure of the opening in the fixing member from the knee joint.

The material of the "patella fixing member" is preferably made of silicon rubber, and that of the fixing member "pressing band" is preferably of some stretchable fabric, but other fabric may also be used.

DETAILED DESCRIPTION OF THE INVENTION

Figure 1:
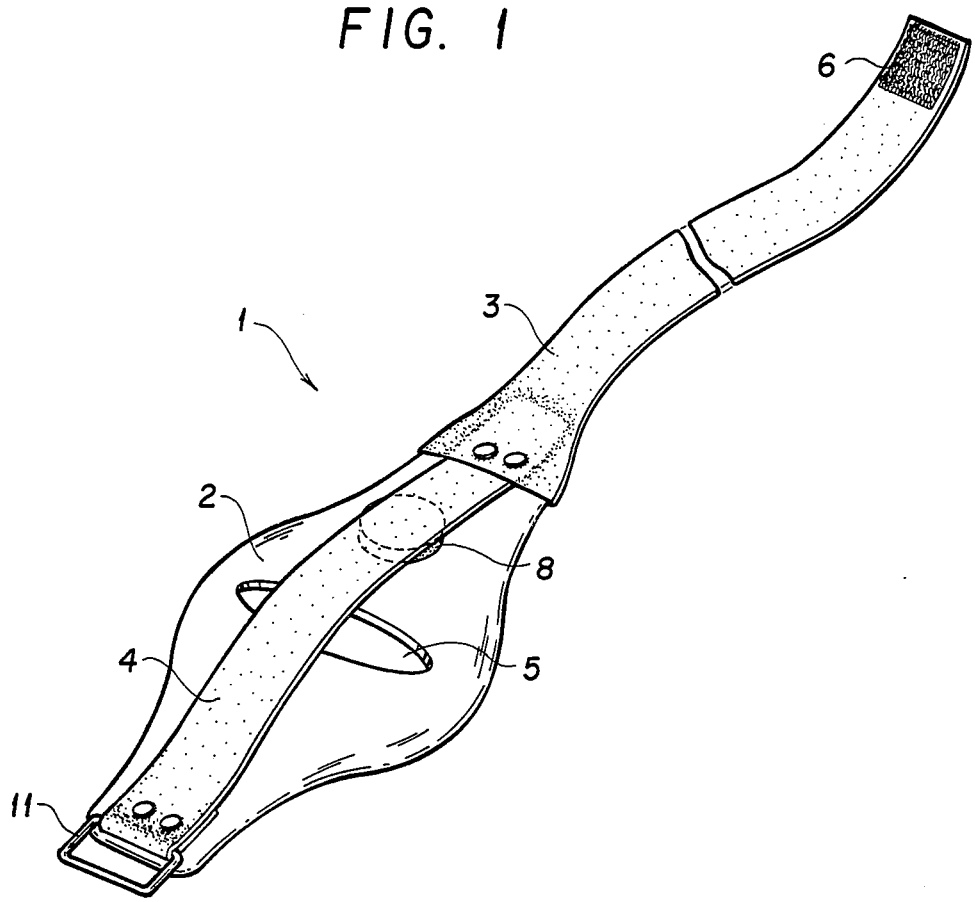
FIG. 1 is a perspective view showing an embodiment of the patella brace with its belt pressing member according to the invention.

The present invention will be described further in details with reference made to the embodiments shown in the drawings:

As illustrated in FIG. 1, the patella brace with its belt pressing member according to the invention comprises a patella fixing member 2 made of silicone rubber, a connecting belt 3 attached to one end of the patella fixing member 2, and a patella-fixing-member pressing band 4 stretched on the top side of the patella fixing 2. It is small in size and very light in weight, and provided with an elliptical opening 5 in the center of the patella fixing member 2.

To put on this brace, apply the opening 5 to the patella position, wind the connecting belt 3 around the rear of the leg, and after passing its end through a rectangular retaining ring 11, let the plane zipper 6 on the end of the connection belt 3 be engaged with the connecting belt 3, while stretching the belt so that an adequate pressure is applied on the affected part.

Figure 2:
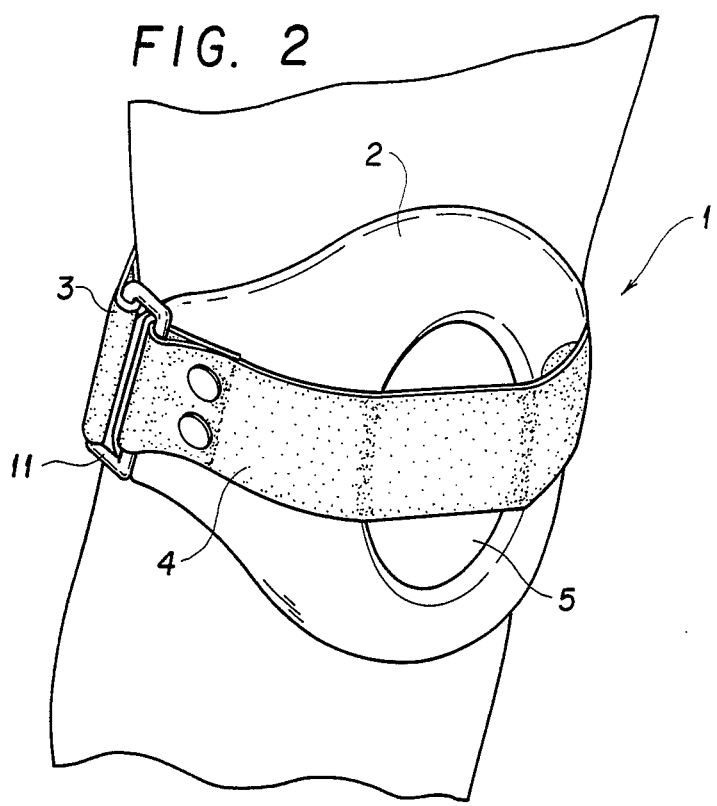
FIG. 2 is a perspective view showing the condition of the patella brace with its belt pressing member shown in FIG. 1 when it is put on the left foot.

FIG. 2 shows the condition when the patella brace 1 in FIG. 1 is put on the left knee joint by the above procedure.

Tightening by the connecting belt 3 applies uniform pressure on the knee joint and fixes the brace on the knee joint, and the silicone rubber allows little slippage of the brace. The opening 5 assumes an elliptical shape in its natural condition, but takes a nearly round shape fitting to the patella, when put on the knee, by being deformed by the stretching of the connecting belt 3. Here, the fixing member pressing band 4 provided on the top side of the patella fixing member 2 is stretched along with the deformed fixing member 2, and thereby presses down the patella fixing member 2 against the knee joint. Had the fixing member pressing band 4 not been present, the opening 5 would be deformed when the knee joint is bent, resulting in decreased effectiveness of the device.

Figure 3:
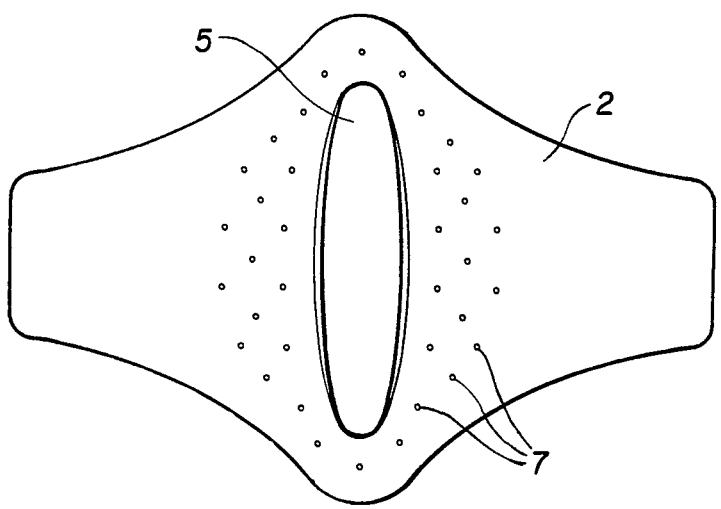
FIG. 3 is a plan view showing another embodiment of said patella brace.

The use of silicone rubber as the patella fixing member 2 prevents the slippage between the skin surface and elevates the patella holding property. It is also an advantage that the silicone rubber has some hygroscopicity. If any mustiness by perspiration is apprehended, it can be overcome by providing many small pores as shown in FIG. 3.

Figure 4A:
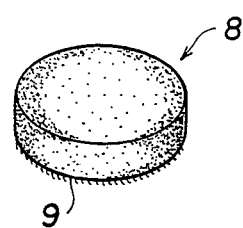
FIG. 4(a) is a perspective view and FIG. 4(b) is a plan view showing an embodiment of the patella pressing patch.
Figure 4B:
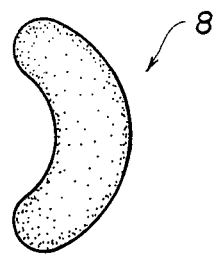
Figure 5:
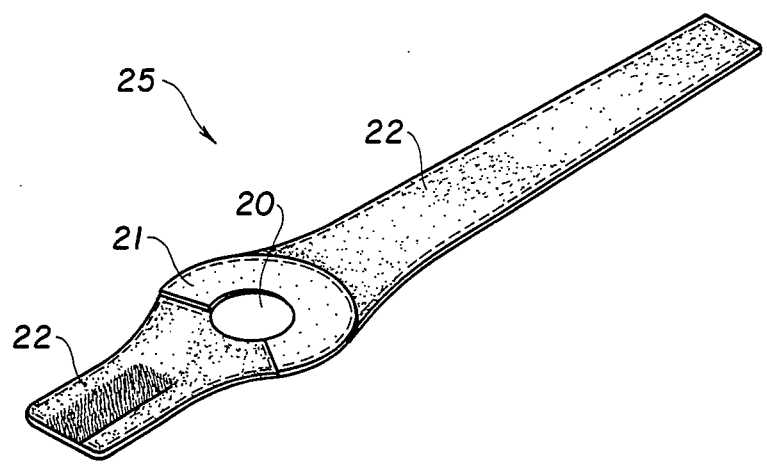
FIG. 5 is a perspective view showing the patella brace of the prior art.

On the bottom side of the fixing member pressing band 4, a patella pressing patch 8 is provided. This is made of a plastic foam on one side with a plane zipper 9 provided on the other, so that patch 8 can be to the required position on the bottom face of the fixing member pressing band 4. The configuration of the patella pressing patch 8 may be disk-like as shown in FIG. 4(a) or may have a cavity as shown in FIG. 4(b) to enhance the patella holding property.

As described in detail above, the patella brace with its belt pressing member according to the invention is provided on the top side of the patella fixing member with a patella fixing member pressing band along the longitudinal direction of the connecting belt, and on the bottom side of the fixing member pressing band with a patella pressing patch. It has such advantages that the feel of incompatibility is slight even when it is worn for a long period, being small in size and light in weight and easy to put on and take off, and that the pressure applied in the direction to correct the dislocated patella is not impaired by the bending and stretching of the knee. Because of its highly protective, pain removing, and therapeutical effects, the patella brace in accordance with the invention has a wide range of applications, including as a supporter in sports.

What is claimed is:

1. A therapeutic apparatus to be worn on the leg for the protection of the patella, the correction of patella maladies and the relief of pain resulting therefrom, comprising:
    an elastic patella fixing member having front and rear surfaces said patella fixing member having an opening positioned to coincide with and fit over the patella;
    a connecting belt extending laterally from said fixing member and constructed so as to be capable of being wound and secured around the knee joint;
    a pressing band overlying the front surface of the patella fixing member and the opening therein and extending along the direction of the connecting belt; and
    a patella pressing patch on the rear surface of the pressing band in a position laterally of said patella fixing member opening
    said apparatus being applied so that said fixing member coincides with the patella and said belt is secured around said knee joint, said opening being fitted over the patella to support the same and said pressing patch providing lateral support to the patella through said pressing band.

2. A patella apparatus in accordance with claim 1, wherein said patella fixing member is made of silicone rubber bent in the shape of a cup.

3. A patella apparatus in accordance with claim 1, wherein said pressing band is stretchable in its lateral direction.

4. A patella apparatus in accordance with claim 1, wherein said patella pressing patch is detachably and movable attached to the rear surface of the pressing band.

5. A patella apparatus as claimed in claim 2, wherein an elliptical opening is provided in the patella fixing member so that said opening may become nearly round by stretching when the patella brace is applied to the knee.

6. A patella apparatus in accordance with claim 2 wherein said fixing member pressing band is stretchable in its lateral direction.

7. A patella apparatus in accordance with claim 3 wherein said patella pressing patch is detachably and movable attached to the rear surface of the fixing member pressing band.

8. A patella apparatus as claimed in claim 1 wherein an elliptical opening is provided in the patella fixing member so that said opening may become nearly round by stretching of the fixing member when the patella brace is put on the knee.

9. A patella apparatus as claimed in claim 3 wherein an elliptical opening is provided in the patella fixing member so that said opening may become nearly round by stretching of the fixing member when the patella brace is put on the knee.

10. A patella apparatus as claimed in claim 4 wherein an elliptical opening is provided in the patella fixing member so that said opening may become nearly round by stretching of the fixing member when the patella brace is put on the knee.

11. A patella apparatus in accordance with claim 3 wherein said patella pressing patch is detachably and movably attached to the rear surface of the pressing band.

* * * * *